(12) United States Patent
Champagne et al.

(10) Patent No.: US 11,147,681 B2
(45) Date of Patent: Oct. 19, 2021

(54) SMALL BONE ANGLED COMPRESSION SCREW

(71) Applicant: ExsoMed Corporation, Phoenix, AZ (US)

(72) Inventors: Lloyd P. Champagne, Phoenix, AZ (US); Jozef Zoldos, Paradise Valley, AZ (US)

(73) Assignee: ExsoMed Corporation, Aliso Viejo, CA (US)

( * ) Notice: Subject to any disclaimer, the term of this patent is extended or adjusted under 35 U.S.C. 154(b) by 97 days.

(21) Appl. No.: 16/122,264

(22) Filed: Sep. 5, 2018

(65) Prior Publication Data
US 2019/0070013 A1 Mar. 7, 2019

Related U.S. Application Data

(60) Provisional application No. 62/554,130, filed on Sep. 5, 2017.

(51) Int. Cl.
*A61F 2/42* (2006.01)
*A61B 17/86* (2006.01)
(Continued)

(52) U.S. Cl.
CPC ........ *A61F 2/4241* (2013.01); *A61B 17/7225* (2013.01); *A61B 17/7291* (2013.01); *A61B 17/8615* (2013.01); *A61B 17/8635* (2013.01); *A61B 17/863* (2013.01); *A61B 17/8605* (2013.01); *A61B 2017/681* (2013.01); *A61F 2002/30156* (2013.01);
(Continued)

(58) Field of Classification Search
CPC ........ A61F 2/42; A61F 2/4241; A61F 2/2425; A61F 2002/4228; A61F 2002/4233; A61F 2002/4243; A61F 2002/4251; A61F 2002/4253; A61F 2002/4256; A61F 2002/4258; A61B 17/7208; A61B 17/7225; A61B 17/842; A61B 17/7283; A61B 17/7291; A61B 17/8615; A61B 17/862; A61B 17/863
See application file for complete search history.

(56) References Cited

U.S. PATENT DOCUMENTS

| 1,741,279 A | 12/1929 | Bowman |
| 2,037,586 A | 4/1936 | Olson |

(Continued)

FOREIGN PATENT DOCUMENTS

| CH | 643131 | 5/1984 |
| CH | 646858 | 12/1984 |

(Continued)

*Primary Examiner* — Alvin J Stewart
(74) *Attorney, Agent, or Firm* — Knobbe, Martens, Olson & Bear, LLP

(57) ABSTRACT

The present invention relates to a device and system for surgical fixation of small bones, small bone fragments, and osteotomies and more particularly to compression screw having a threaded leading portion which is joined to a section that is free from threads, and which includes an angle or from 12° to 25° in a plane through the longitudinal axis of the screw and a portion which is joined to a head having a configuration that is intended to provide anti-rotational stability and compression through the device.

15 Claims, 3 Drawing Sheets

(51) Int. Cl.
*A61B 17/72* (2006.01)
*A61B 17/68* (2006.01)
*A61F 2/30* (2006.01)

(52) U.S. Cl.
CPC .............. *A61F 2002/30205* (2013.01); *A61F 2002/30224* (2013.01); *A61F 2002/30322* (2013.01); *A61F 2002/30622* (2013.01); *A61F 2002/4243* (2013.01)

(56) References Cited

U.S. PATENT DOCUMENTS

| | | | |
|---|---|---|---|
| 2,210,455 A | 8/1940 | Hosking | |
| 2,217,951 A | 10/1940 | Hosking | |
| 2,229,892 A | 1/1941 | Hosking | |
| 2,242,003 A | 5/1941 | Lorenzo | |
| 3,275,055 A | 9/1966 | Gutshall | |
| 3,397,699 A | 8/1968 | Kohl | |
| 3,717,146 A | 2/1973 | Halloran | |
| 4,016,874 A | 4/1977 | Maffei | |
| 4,175,555 A | 11/1979 | Herbert | |
| 4,380,414 A | 4/1983 | Capuano | |
| 4,463,753 A | 8/1984 | Gustilo | |
| 4,471,777 A | 9/1984 | McCorkle | |
| 4,584,722 A | 4/1986 | Levy et al. | |
| 4,608,965 A | 9/1986 | Anspach | |
| 4,764,066 A | 8/1988 | Terrell | |
| 4,781,191 A | 11/1988 | Thompson | |
| 4,812,095 A | 3/1989 | Piacenti | |
| 4,901,717 A | 2/1990 | Moore et al. | |
| 4,909,789 A | 3/1990 | Taguchi et al. | |
| 5,061,283 A | 10/1991 | Silvestrini | |
| 5,074,790 A * | 12/1991 | Bauer | A61C 8/0075 |
| | | | 433/174 |
| 5,234,299 A | 8/1993 | Giannuzzi | |
| 5,312,255 A * | 5/1994 | Bauer | A61C 8/0012 |
| | | | 433/173 |
| 5,345,927 A | 9/1994 | Bonutti | |
| 5,443,466 A | 8/1995 | Shah | |
| 5,645,545 A | 7/1997 | Bryant | |
| 5,667,510 A | 9/1997 | Combs | |
| 5,690,633 A | 11/1997 | Taylor et al. | |
| 5,853,413 A | 12/1998 | Carter et al. | |
| 6,001,101 A | 12/1999 | Augagneur et al. | |
| 6,019,762 A | 2/2000 | Cole | |
| 6,187,007 B1 | 2/2001 | Frigg | |
| 6,221,006 B1 | 4/2001 | Dubrul et al. | |
| 6,231,319 B1 | 5/2001 | Iida et al. | |
| 6,231,413 B1 | 5/2001 | Tsukamoto | |
| 6,306,140 B1 * | 10/2001 | Siddiqui | A61B 17/863 |
| | | | 606/315 |
| 6,319,254 B1 | 11/2001 | Giet et al. | |
| 6,475,242 B1 | 11/2002 | Bramlet | |
| 6,517,541 B1 | 2/2003 | Sesic | |
| 6,592,623 B1 | 7/2003 | Bowlin et al. | |
| 6,607,530 B1 | 8/2003 | Carl et al. | |
| 6,808,526 B1 | 10/2004 | Magerl et al. | |
| 7,041,106 B1 * | 5/2006 | Carver | A61B 17/7291 |
| | | | 606/309 |
| 7,334,976 B2 | 2/2008 | Dicke | |
| 7,465,135 B2 | 12/2008 | Fritsch | |
| 7,507,242 B2 | 3/2009 | Triplett et al. | |
| 7,708,738 B2 | 5/2010 | Fourcault et al. | |
| 7,766,942 B2 | 8/2010 | Patterson | |
| 7,988,724 B2 | 8/2011 | Salahieh et al. | |
| 8,011,866 B2 | 9/2011 | Harris | |
| 8,105,367 B2 | 1/2012 | Austin et al. | |
| 8,118,849 B2 | 2/2012 | Wahl et al. | |
| 8,157,803 B1 | 4/2012 | Zirkle, Jr. | |
| 8,398,687 B2 | 3/2013 | Vasta et al. | |
| 8,398,690 B2 | 3/2013 | Bottlang et al. | |
| 8,414,648 B2 | 4/2013 | Reiley | |
| 8,419,776 B2 | 4/2013 | Prandi et al. | |
| 8,518,042 B2 | 8/2013 | Winsow et al. | |
| 8,568,462 B2 | 10/2013 | Sixto et al. | |
| 8,597,337 B2 * | 12/2013 | Champagne | A61B 17/863 |
| | | | 606/309 |
| 8,608,783 B2 | 12/2013 | Graham et al. | |
| 8,734,462 B2 | 5/2014 | Reiley et al. | |
| 8,814,918 B2 | 8/2014 | Orbay et al. | |
| 8,852,253 B2 | 10/2014 | Mafi | |
| 8,864,804 B2 * | 10/2014 | Champagne | A61B 17/863 |
| | | | 606/309 |
| 8,888,429 B2 | 11/2014 | Pamer | |
| 8,906,075 B2 | 12/2014 | Conley et al. | |
| 8,945,193 B2 | 2/2015 | Kirschman | |
| 9,011,505 B2 | 4/2015 | Prandi et al. | |
| 9,017,404 B2 | 4/2015 | Champagne et al. | |
| 9,046,120 B2 | 6/2015 | Phua | |
| 9,078,716 B2 | 7/2015 | Pech | |
| 9,175,715 B2 | 11/2015 | Babej | |
| 9,265,600 B2 | 2/2016 | Niese | |
| 9,480,515 B2 | 11/2016 | Champagne | |
| 9,482,260 B1 * | 11/2016 | Krause | A61B 17/8625 |
| 9,539,084 B2 | 1/2017 | Champagne | |
| 9,642,656 B2 | 5/2017 | Kotuljac et al. | |
| 9,687,284 B2 | 6/2017 | Pancheco et al. | |
| 9,724,140 B2 | 8/2017 | McCormick | |
| 9,848,927 B2 | 12/2017 | Giorno | |
| 9,861,413 B2 * | 1/2018 | Palmer | A61B 17/863 |
| 9,980,759 B2 | 5/2018 | Lavi | |
| 10,058,368 B2 | 8/2018 | Orbay et al. | |
| 10,080,597 B2 | 9/2018 | Shemwell et al. | |
| 10,098,680 B2 | 10/2018 | Champagne | |
| 10,136,929 B2 * | 11/2018 | Fallin | A61B 17/7291 |
| 10,245,091 B2 | 4/2019 | Champagne et al. | |
| 10,499,960 B2 * | 12/2019 | Sinnott | A61B 17/7233 |
| 10,610,276 B2 | 4/2020 | Lutz | |
| 2001/0049529 A1 | 12/2001 | Cachia et al. | |
| 2002/0045897 A1 | 4/2002 | Dixon et al. | |
| 2002/0055747 A1 | 5/2002 | Cano et al. | |
| 2002/0055749 A1 | 5/2002 | Esnouf et al. | |
| 2002/0143337 A1 | 10/2002 | Orbay et al. | |
| 2002/0198527 A1 | 12/2002 | Muckter | |
| 2003/0014077 A1 | 1/2003 | Leung | |
| 2003/0083661 A1 | 5/2003 | Orbay et al. | |
| 2003/0130735 A1 | 7/2003 | Rogalski | |
| 2004/0193217 A1 | 9/2004 | Lubbers | |
| 2004/0210227 A1 * | 10/2004 | Trail | A61B 17/863 |
| | | | 606/916 |
| 2004/0260288 A1 | 12/2004 | Means | |
| 2005/0075642 A1 | 4/2005 | Felt | |
| 2005/0085824 A1 | 4/2005 | Castaneda | |
| 2005/0107791 A1 | 5/2005 | Manderson | |
| 2005/0143735 A1 | 6/2005 | Kyle | |
| 2006/0129153 A1 | 6/2006 | Klaue et al. | |
| 2006/0149249 A1 | 7/2006 | Mathoulin et al. | |
| 2006/0165506 A1 | 7/2006 | Panasik | |
| 2006/0195099 A1 | 8/2006 | Bottlang | |
| 2006/0271061 A1 | 11/2006 | Beyar | |
| 2006/0276790 A1 | 12/2006 | Dawson | |
| 2007/0027547 A1 | 2/2007 | Rydell et al. | |
| 2007/0135816 A1 | 6/2007 | Kropf et al. | |
| 2007/0233123 A1 | 10/2007 | Ahmad et al. | |
| 2007/0282342 A1 | 12/2007 | Niederberger et al. | |
| 2007/0299449 A1 | 12/2007 | Allinniemi et al. | |
| 2008/0183220 A1 | 7/2008 | Glazer | |
| 2008/0219801 A1 | 9/2008 | Toenjes | |
| 2008/0249547 A1 | 10/2008 | Dunn | |
| 2008/0249574 A1 | 10/2008 | McCombs et al. | |
| 2008/0287958 A1 * | 11/2008 | Logan | A61B 17/921 |
| | | | 606/100 |
| 2008/0300639 A1 | 12/2008 | Martin | |
| 2009/0062868 A1 | 3/2009 | Casutt | |
| 2009/0149890 A1 * | 6/2009 | Martin | A61B 17/1728 |
| | | | 606/316 |
| 2009/0240291 A1 | 9/2009 | Gorek | |
| 2009/0299369 A1 | 12/2009 | Orbay et al. | |
| 2009/0306718 A1 * | 12/2009 | Tipirneni | A61B 17/685 |
| | | | 606/263 |
| 2010/0106254 A1 | 4/2010 | Delsignore | |
| 2010/0121136 A1 | 5/2010 | Champagne | |
| 2010/0130978 A1 | 5/2010 | Orbay et al. | |
| 2010/0174323 A1 | 7/2010 | Fourcault et al. | |

(56) References Cited

U.S. PATENT DOCUMENTS

| | | | |
|---|---|---|---|
| 2010/0211115 A1 | 8/2010 | Tyber et al. | |
| 2010/0312286 A1 | 12/2010 | Dell'Oca | |
| 2010/0312292 A1* | 12/2010 | Tipirneni | A61B 17/685 606/86 R |
| 2010/0324556 A1 | 12/2010 | Tyber et al. | |
| 2011/0009865 A1 | 1/2011 | Orfaly | |
| 2011/0118795 A1 | 1/2011 | Jang | |
| 2011/0130794 A1 | 6/2011 | Vaidya | |
| 2011/0144644 A1* | 6/2011 | Prandi | A61B 17/7233 606/62 |
| 2011/0144703 A1* | 6/2011 | Krause | A61B 17/8625 606/309 |
| 2011/0276095 A1 | 11/2011 | Bar et al. | |
| 2011/0313473 A1 | 12/2011 | Prandi et al. | |
| 2012/0083847 A1* | 4/2012 | Huebner | A61B 17/8057 606/281 |
| 2012/0136398 A1 | 5/2012 | Mobasser | |
| 2012/0191140 A1 | 7/2012 | Bonutti | |
| 2012/0197311 A1 | 8/2012 | Kirschman | |
| 2012/0221104 A1 | 8/2012 | Altman et al. | |
| 2012/0232599 A1 | 9/2012 | Schoenly et al. | |
| 2012/0253464 A1 | 10/2012 | Hwang et al. | |
| 2012/0253465 A1 | 10/2012 | Missos | |
| 2013/0012987 A1 | 1/2013 | Klein et al. | |
| 2013/0053961 A1 | 2/2013 | Darwin et al. | |
| 2013/0060333 A1 | 3/2013 | Gonzalez | |
| 2013/0131699 A1 | 5/2013 | Jiango et al. | |
| 2013/0138123 A1 | 5/2013 | Stone et al. | |
| 2013/0165979 A1 | 6/2013 | Greenberg et al. | |
| 2013/0190872 A1 | 7/2013 | Makower et al. | |
| 2013/0197592 A1 | 8/2013 | Mafi | |
| 2013/0245626 A1* | 9/2013 | Lavi | A61B 17/72 606/62 |
| 2013/0245700 A1 | 9/2013 | Choinski | |
| 2013/0245762 A1 | 9/2013 | Van Kampen et al. | |
| 2013/0261662 A1 | 10/2013 | Mayer et al. | |
| 2013/0274789 A1 | 10/2013 | Brooks et al. | |
| 2013/0274879 A1 | 10/2013 | Champagne et al. | |
| 2013/0282058 A1 | 10/2013 | ElAttrache et al. | |
| 2013/0325011 A1 | 12/2013 | Cleveland et al. | |
| 2014/0025124 A1 | 1/2014 | Champagne et al. | |
| 2014/0067063 A1 | 3/2014 | Bonutti | |
| 2014/0155943 A1 | 6/2014 | Andersen | |
| 2014/0257349 A1 | 9/2014 | Sudekum | |
| 2014/0276846 A1 | 9/2014 | Mauldin | |
| 2014/0309747 A1* | 10/2014 | Taylor | A61B 17/846 623/21.11 |
| 2014/0336712 A1 | 11/2014 | Strnad et al. | |
| 2015/0066060 A1 | 3/2015 | Bojarski | |
| 2015/0094722 A1 | 4/2015 | Champagne et al. | |
| 2015/0094724 A1 | 4/2015 | Champagne et al. | |
| 2015/0094777 A1 | 4/2015 | Champagne et al. | |
| 2015/0173737 A1 | 6/2015 | Champagne et al. | |
| 2015/0182325 A1 | 7/2015 | Champagne et al. | |
| 2015/0201978 A1* | 7/2015 | Piccin | A61B 17/7266 606/63 |
| 2015/0201984 A1 | 7/2015 | Orbay et al. | |
| 2015/0374503 A1* | 12/2015 | Lovick | A61B 17/7291 623/23.5 |
| 2016/0030097 A1* | 2/2016 | Mildner | A61B 17/863 606/304 |
| 2016/0045324 A1* | 2/2016 | Austin | A61B 17/7291 623/21.19 |
| 2016/0213413 A1 | 7/2016 | Hientzsch et al. | |
| 2016/0256290 A1 | 9/2016 | Seavey et al. | |
| 2016/0278833 A1 | 9/2016 | Wong et al. | |
| 2016/0287300 A1 | 10/2016 | Mccormick et al. | |
| 2016/0296263 A1 | 10/2016 | Champagne et al. | |
| 2016/0296264 A1 | 10/2016 | Champagne et al. | |
| 2016/0310187 A1 | 10/2016 | Leibinger et al. | |
| 2016/0338748 A1 | 11/2016 | Champagne et al. | |
| 2017/0014170 A1* | 1/2017 | Fallin | A61B 17/7291 |
| 2017/0027577 A1 | 2/2017 | Kubiak et al. | |
| 2017/0035553 A1 | 2/2017 | Champagne et al. | |
| 2017/0049167 A1 | 2/2017 | Champagne et al. | |
| 2017/0065424 A1 | 3/2017 | Lauf et al. | |
| 2017/0112555 A1 | 4/2017 | Wallenstein et al. | |
| 2017/0151061 A1* | 6/2017 | Lavi | A61F 2/4225 |
| 2017/0189090 A1 | 7/2017 | Champagne et al. | |
| 2017/0196609 A1* | 7/2017 | Champagne | A61B 17/864 |
| 2017/0196612 A1 | 7/2017 | Castaneda et al. | |
| 2017/0239059 A1* | 8/2017 | Boublil | A61F 2/30771 |
| 2017/0319349 A1* | 11/2017 | Kowalczyk | A61F 2/30771 |
| 2017/0325827 A1 | 11/2017 | Champagne et al. | |
| 2018/0008317 A1 | 1/2018 | Sinha | |
| 2018/0021124 A1 | 1/2018 | Champagne et al. | |
| 2018/0049881 A1* | 2/2018 | Austin | A61F 2/30771 |
| 2018/0092677 A1* | 4/2018 | Peterson | A61B 17/7225 |
| 2018/0263669 A1* | 9/2018 | Peterson | A61B 17/86 |
| 2018/0303529 A1 | 10/2018 | Zastrozna | |
| 2018/0317989 A1* | 11/2018 | Sellers | A61B 17/8685 |
| 2019/0070009 A1* | 3/2019 | Champagne | A61B 17/863 |
| 2019/0210016 A1 | 7/2019 | Zhong et al. | |
| 2019/0262047 A1 | 8/2019 | Sommers et al. | |
| 2019/0321087 A1 | 10/2019 | Wapner et al. | |

FOREIGN PATENT DOCUMENTS

| | | |
|---|---|---|
| DE | 2713386 | 11/1978 |
| DE | 102007003645 | 7/2008 |
| DE | 2020131101135 U1 | 7/2014 |
| EP | 0597223 | 5/1994 |
| EP | 1378205 | 1/2004 |
| EP | 2606843 | 6/2013 |
| GB | 2007099 | 5/1979 |
| GB | 2181356 | 4/1987 |
| WO | 9733537 A1 | 9/1997 |
| WO | 2004093700 A1 | 11/2004 |
| WO | 2005092226 A1 | 10/2005 |
| WO | 2006105935 A1 | 10/2006 |
| WO | WO 2007/081601 | 7/2007 |
| WO | 2007109140 A1 | 9/2007 |
| WO | WO 2008/063156 | 5/2008 |
| WO | WO 2010/151589 | 12/2010 |
| WO | WO 2012/050424 | 4/2012 |
| WO | WO 2014/011933 | 1/2014 |
| WO | WO 2014/089522 | 6/2014 |
| WO | WO 2015/050895 | 9/2015 |
| WO | WO 2015/050896 | 9/2015 |
| WO | WO 2015/050898 | 9/2015 |
| WO | WO 2015/050900 | 9/2015 |
| WO | WO 2015/050902 | 9/2015 |
| WO | WO 2016/186847 | 11/2016 |

* cited by examiner

SMALL BONE ANGLED COMPRESSION SCREW

FIELD OF THE INVENTION

The present invention relates to a device and system for surgical fixation of small bones, small bone fragments, and osteotomies and more particularly to compression screw having a threaded leading portion which is joined to a section that is free from threads, and which includes an angle or arc from 12° to 25° in a plane through the longitudinal axis of the screw and a trailing portion which is joined to a head having a configuration that is intended to provide anti-rotational stability and compression through the device.

BACKGROUND OF THE INVENTION

Patients often suffer from late stage arthritis in phalangeal joints of the hands and feet, and this presents a variety of challenges for attending physicians. While current treatment protocols usually provide acceptable results, there is a likelihood of straight distal interphalangeal joint fusion which provides for sub-optimal outcomes. Research has shown that when a patient's distal interphalangeal joint is fused in a functional position, finger dexterity and grip strength improve over that of a patient with a straight fusion. Physicians can achieve angled fusions by using k-wire fixation, however, this immobilization protocol can fail, and lead to several complications and varied results. While the utilization of compression screws can provide reliable, strong repairs, it does not offer the additional benefit of function flexion which is provide by a properly angled and oriented implant fixation device, especially one, which provides the added benefit of compression across the joint during fusion.

Advantageous locations the use of the present invention is in the phalanges of the hand or foot. In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint. The joints are covered on the ends with articular cartilage. The foot has an analogous structure substituting the large toe for the thumb. It should be understood that there may be additional surgical techniques or locations in the body where the device of the present invention may be suitable for use

SUMMARY OF THE INVENTION

The present invention solves the problems associated with performing a fusion technique or an osteotomy, in particular in the interphalangeal joints. The device of the invention is a compression screw having a leading portion including a beveled and/or fluted self-tapping cutting tip, and a threaded portion, and an intermediate shaft portion which joins the trailing portion and forms an angle of from 12° to 25°, and preferably 18°+/−3°. Moreover, the intermediate shaft portion is joined to a trailing head portion that is configured to provide for compression across the fusion joint, and to inhibit rotation of the compression device in the interphalangeal position. The head is specifically configured (in a modified truncated triangular shape including hemi-cylindrical longitudinal flange members or alternatively, a tapered conical shape having threads) to be inserted into the bone without damaging the bone because it is sized and shaped to support the bone from the inside and to fit in the narrow confines of the intramedullary channel of these bones, to provide a head design which provides compression across the joint, but which can be seated below the surface of the bone to avoid screw prominence on the digit tip or intrusion into the fat pad of the finger or toe and the irritation that can result from a proud portion. In addition, the present invention provides for a percutaneous insertion in a surgical technique with an intramedullary implant designed to minimize soft tissue, cartilage and vascular damage upon insertion; and to facilitate early, active mobilization post-operative protocols for accelerated healing and earlier return to work.

The head at the trailing end includes a driving recess, such as a hexalobe, capable of being driven by a suitable driver into the opening.

DETAILED DESCRIPTION OF THE INVENTION

Figure 1:
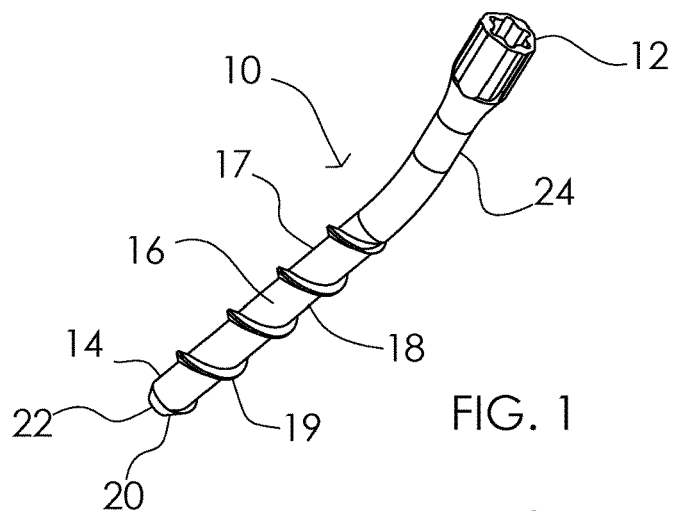
FIG. 1 is an isometric view of a device in accordance with the invention.
Figure 2:
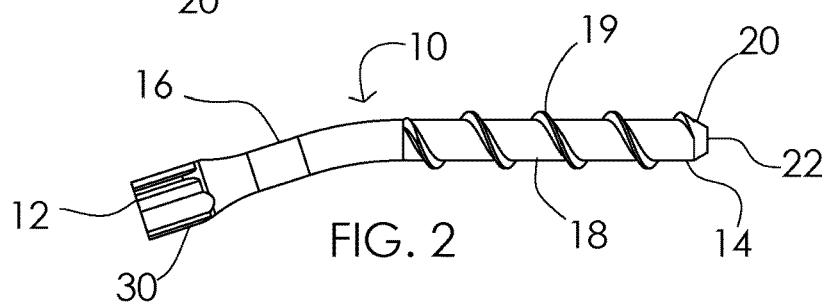
FIG. 2 is a side view of the device of FIG. 1.
Figure 3:
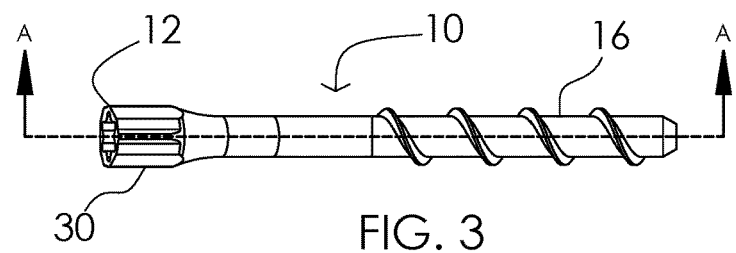
FIG. 3 is a side view of the device of FIG. 1 taken at a rotation of 90° to the view in FIG. 2.
Figure 4:
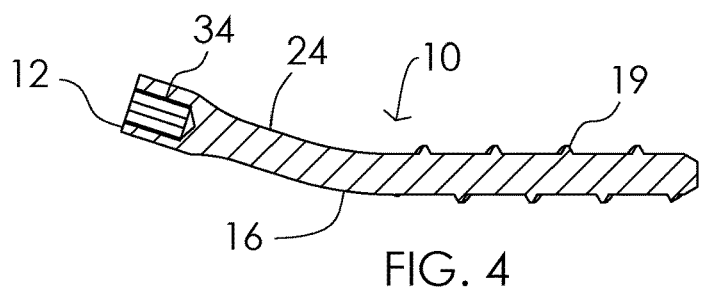
FIG. 4 is a cross-section of the device of FIG. 3 taken along line A-A.

FIG. 1 shows an exemplary embodiment 10 of the angled compression screw of the present invention. The screw 10 may be formed of any suitable biocompatible material, such as surgical grade stainless steel, titanium, alloys of nickel and chromium, nitinol, PEEK, hydroxyapatite, bio-glass or other bio compatible materials or combinations of these materials. The screw 10 has a first end, or trailing end, 12, a second end, or leading end, 14, a shaft 16 with an outer surface 17, and the shaft 16 including a leading portion 18 which includes a thread 19 and has a beveled cutting tip 20 at the terminal end 22. The leading portion 18 is joined to a trailing portion 24 of the shaft 16. It should be noted while that the trailing portion may be considered to be proximal to the leading portion relative to the screw itself, in use, the leading portion is intended to be implanted more proximally in the joint than the trailing portion. The leading portion includes an intermediate angled area that joins the leading portion 18 of the shaft to a compression head 30 which has a driving surface 32 in a drive recess 34 formed in the top of first end 12. The angle of the angled area is from 10° to 25°, and preferably 18°+/−3° which is defined at the intersection of the central longitudinal axes of the trailing portion and the leading portions of the shaft. Accordingly, the outer surfaces of the angled portion include a slight radius. The shaft is only angled in a single plane as can be seen in a comparison of FIG. 2 and FIG. 3.

In the first embodiment, the cutting end 20 includes a bevel and a counterbore that helps to cut through any bone left behind when the bone is drilled to receive device 10, and further provides a space to receive extraneous material dragged along during insertion. The driving surface 32 in this embodiment has a hexalobe drive configuration, although any suitable driving configuration may be used. Other driving configurations that may be used include slotted, Pozidriv, Robertson, tri-wing, Torq-Set, Spanner-Head, Triple Square and hex head.

Figure 5:
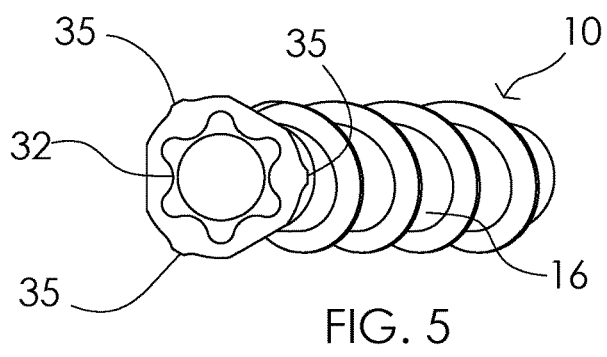
FIG. 5 is a detail of FIG. 1 showing the end view of the head of the device from the top.

In the first embodiment, the head of the compression screw 30 has a profile as seen from the top in FIG. 5 that represents a truncated modified triangle. In particular, the tips of the angle of the triangle are rounded slightly and instead include hemi-cylindrical flanges 35, that serve to strengthen the head 30 in areas where the torque driving recess has been cut-out, and further which helps to inhibit the distal flange from rotating. The configuration is radially symmetrical geometric shape (here a modified triangle as described below), but irregular, meaning that it is a circle of a diameter that is larger than the radius of the arc prescribed by the bent shaft rotated about a circle, or slightly larger than the size of the intermutually channel. Then, from 2-5 flat surfaces are designed in the circle, and optimally three flats to carve a triangular shape, and the flats can additionally include other protrusions, such as the hemi-cylindrical flanges in order to better wedge the head into position in the intramedullary channel of the distal phalange to secure it in place and inhibit rotation relative to the intermediate flange. Optionally, the terminal area of the head can flare or widen in cross-section in order to enhance the compression.

The leading portion of the device includes a thread 19 which is defined between the outer diameter and the inner diameter and can suitably include a right handed single start thread with a pitch of from 3-4, and preferably at 3+/−0.5 with a similar lead value. The leading and following profiles of the threads together form an angle of 60°+/−15°, and preferably 10°, and with a thread depth of 0.1 mm to 0.4 mm, and optionally a thrust profile or buttress profile.

Figure 6:
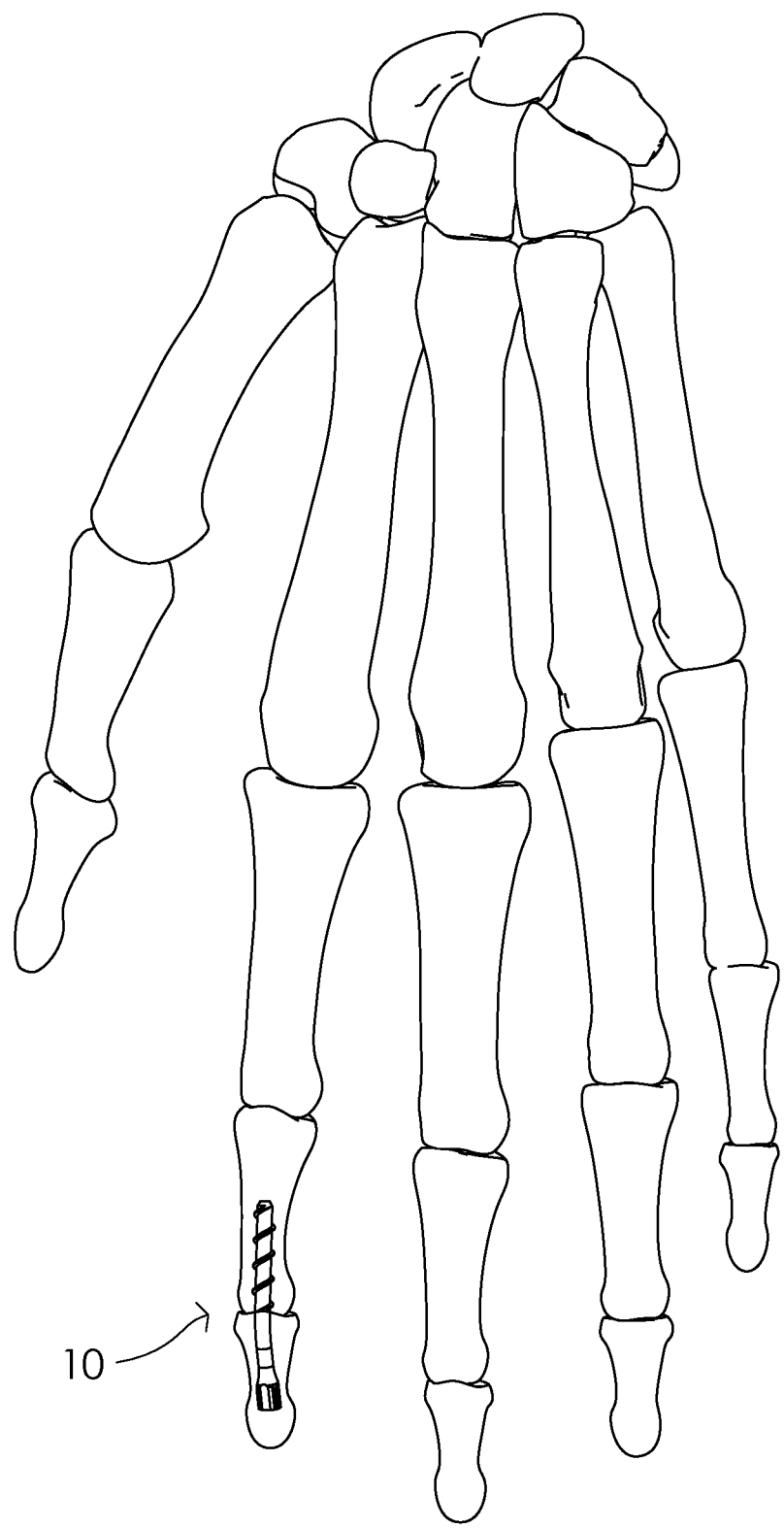
FIG. 6 is a dorsal view of a skeleton of a hand showing the implant of the invention in place in a PIP fusion.

FIG. 6 illustrates a screw 10 in accordance with the present invention in position across a first PIP joint to secure a fusion.

Figure 7:
FIG. 7 is an illustration of the step of inserting a guide wire in a retrograde fashion to align the distal and intermediate phalanges in accordance with the technique of the invention.
Figure 8:
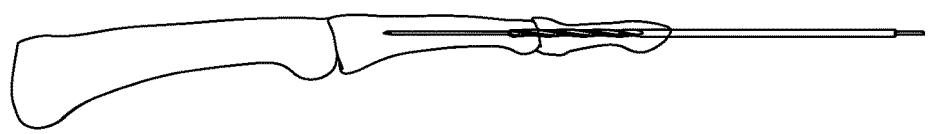
FIG. 8 is an illustration of the step of drilling by passing a cannulated drill over the guide wire.

In FIG. 7, in a first step of a surgical technique in accordance with the invention, the joint is scored for fusion and a k-wire is inserted in the intramedullary cannel in retrograde until is abuts the inners cortical surface of the phalanges, In FIG. 8 a cannulated drill 3, uses the K-wire as a guide to drill an opening (i.e., a straight opening or hole) into the phalanges extending through the fracture and providing enough space on each side of the fracture to properly position device 10.

Figure 9:
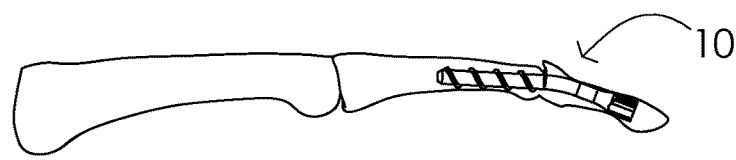
FIG. 9 is an illustration of the step of inserting and confirming the placement of the implant across the fusion site in accordance with the surgical technique of the invention.

In FIG. 9, the device 10 is driven into the opening in the phalanges by means of the drive recess. The outer diameter of the threads 28, is slightly larger than the inner diameter of the opening in the bone. This provides bone material for threads 28 to thread into and provides a tight fit for device 10. Further, the device is configured to allow a bent angled screw to be screwed into a straight hole which has been provided in the cancellous portion of the bone and across a fusion site, but where the device includes an angle along its long axis so that the relationship of the bones, or bone segments is changed as the device is screwed into the hole. Specifically, the device includes an angle in one plane about its long axis which is between 10° and 25°, and more specially which is 18°+/−3°. This angle is defined by the intersection of the axes along the central long axis of the device, and further where the device includes a leading length and a trailing length each extending from the intersection to the termination of the device (i.e. the lateral surfaces at the leading tip and the area surrounding the torque driving recess), where the trailing length describes an arc of rotation when it is rotated about the long axis which describes an arc of rotation diameter that is not larger than, or equal to a cross-sectional diameter of the head of the device below any additional trailing compression feature. Again, this means that the head has a configuration in the cross-section taken transverse to the long axis which is a modified regular geometric shape, such as a circle or an oval that has a maximum size that fill not exceed the space in the bone from external cortical surface to external cortical surface, but which can be "dragged" through the bone in rotation as the threaded leading portion of the screw is screwed into the bone, but which allows the cancellous bone to fill in during healing. Thus, the head has a capability to fill the canal of the bone that is created by the passing of the bent section in order to create compression in addition to having an the anti-rotation aspect which inhibits the device or the bone from rotating from the intended angled orientation (so that an oddly angled phalange is avoided while the desired fusion angle is preserved). This feature is governed by the largest diameter section of the head in contrast to the cuts or flats that create the anti-rotation feature.

It is noted that the head could include a trailing flared portion which exceeds the more leading area in order to increase the feature of compression, and that this trailing flare has a depth along the long axis from the trailing end of the head of less than ½, and more preferably ¼ of the total length of the head. Thus, the head can be dragged into the bone, (which can include a counter-bored portion) without splitting the bone, and will seat below the cortical surface of the bone.

Figure 10:
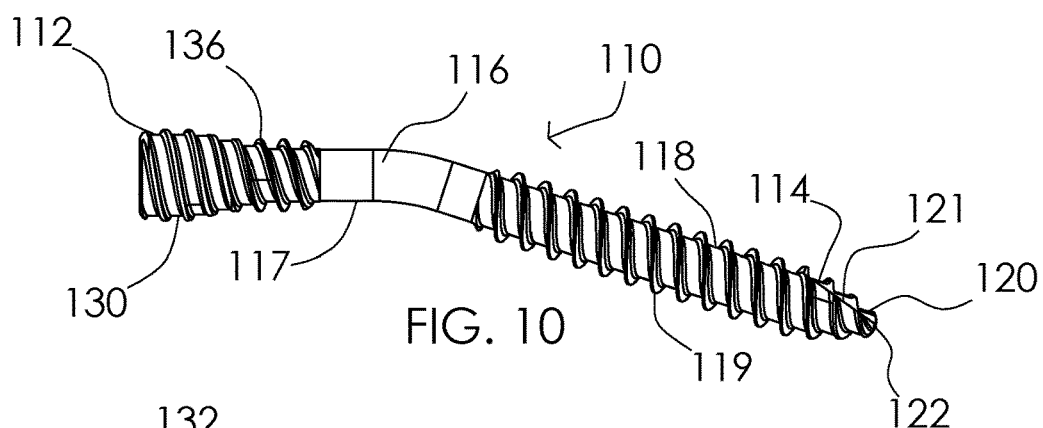
FIG. 10 is an isometric view of a second embodiment of the device in accordance with the invention.
Figures 11, 12:
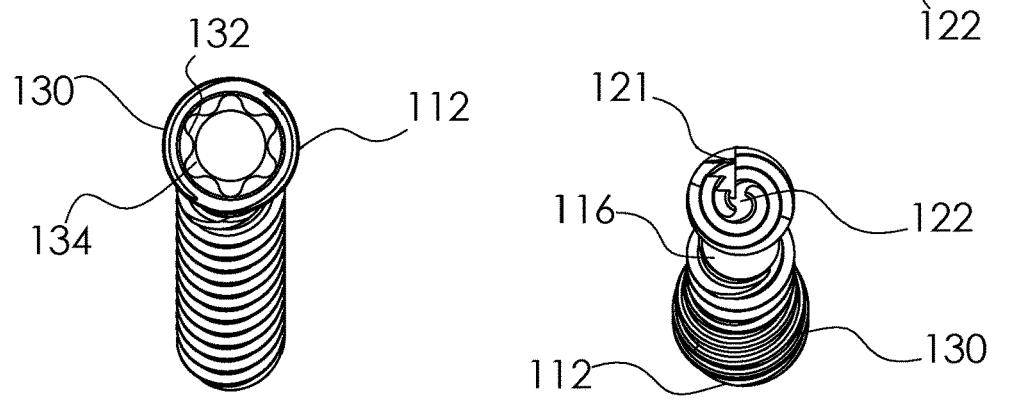
FIG. 11 is an end view of the device of FIG. 10 taken from a first end.
FIG. 12 is an end view of the device of FIG. 10 taken from the second end.

FIGS. 10-12 show a second embodiment of the invention which is similar to the first embodiment, except that the head is a more traditional tapered or conical shape and is threaded in a double lead thread of the same thread shape and pitch value or even a lower pitch value (i.e. 50% to 95%, and preferably 75% to 90% of the pitch value) as the leading portion of the screw. The screw 110 has a first end, or trailing end, 112, a second end, or leading end, 114, a shaft 116 with an outer surface 117, and the shaft 116 including a leading portion 118 which includes a thread 119 and has a tapered cutting tip 120, including a cutting flute 121 at the terminal end 122. The leading portion 118 is joined to a trailing portion 124 of the shaft 116 The trailing portion includes an intermediate angled area that joins the leading portion 118 of the shaft to a tapered or conical compression head 130 with a thread 136 and which has a driving surface 132 in a drive recess 134 formed in the top of first end 112.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A compression screw for use in an angled fusion procedure in the intramedullary channel of a bone, the screw comprising:
   a leading portion having a length and a central longitudinal axis, the leading portion comprising a cutting tip;
   a lag portion which extends from the leading portion and includes a bend from the central longitudinal axis of the leading portion, wherein the lag portion has a length that is from ¼ to ½ of a total length of the lag and leading portions; and
   a head member extending from the lag portion, the head member comprising a torque driving recess and an anti-rotation feature that includes a modified triangle,
   wherein the screw includes a single thread extending along the leading portion and terminating prior to the bend, and
   wherein the bend of the lag portion defines an arc of rotation when the compression screw is rotated about the central longitudinal axis, a maximum diameter of the head being larger than or equal to a diameter of the arc of rotation.

2. A compression screw as set forth in claim 1 wherein the modified triangle comprises a separated plurality of flats.

3. A compression screw as set forth in claim 2 wherein the head has three flats which are separated from one another by a hemi-cylindrical flange.

4. A compression screw as set forth in claim 1 wherein the modified triangle comprises flat surfaces that extend in the direction of the longitudinal axis of the screw and wherein the screw head is radially symmetrical.

5. A method of performing a bent angle bone fusion comprising the steps of:
   drilling a straight hole in a first bone or bone segment and a second bone or bone segment aided by at least a K-wire;
   removing the K-wire from the straight hole; and
   screwing a bone screw in a bent configuration in the straight hole after removing the K-wire from the straight hole, the bone screw comprising a threaded leading portion, an intermediate portion including a bend at an angle with a longitudinal axis of the leading portion, and a head which extends from the intermediate portion and comprises a torque driving feature, wherein the bone screw is advanced into the straight hole in one direction along a longitudinal axis of the straight hole.

6. A method of performing a bent angle bone fusion as set forth in claim 5 wherein the head is configured to allow the leading portion and the intermediate portion prior to the bend to be screwed into the straight hole, wherein after the bone screw is screwed into the straight hole, the bone screw causes compression between the first bone or bone segment and the second bone or bone segment.

7. A method of performing a bent angle bone fusion as set forth in claim 6 wherein the head further comprises an anti-rotation feature.

8. A method of performing a bent angle bone fusion as set forth in claim 7 wherein the anti-rotation feature comprises a modified cylinder or a cone which further includes a plurality of flat surfaces that extend in the direction of the longitudinal axis of the screw.

9. A method of performing a bent angle bone fusion as set forth in claim 7 wherein the head includes external threads.

10. A method of performing a bent angle bone fusion as set forth in claim 6 wherein the head includes external threads.

11. A method of performing a bent angle bone fusion as set forth in claim 5 wherein the head includes external threads.

12. A compression screw for use in an angled fusion procedure in the intramedullary channel of a bone, the screw comprising:
    a leading portion having a length and a central longitudinal axis, the leading portion comprising a cutting tip;
    a lag portion which extends from the leading portion and includes a bend from the central longitudinal axis of the leading portion; and
    a head member extending from the lag portion, the head member comprising a torque driving recess and an anti-rotation feature that includes a modified triangle,
    wherein the screw includes a single thread extending along the leading portion and terminating prior to the bend, and
    wherein the bend of the lag portion defines an arc of rotation when the compression screw is rotated about the central longitudinal axis, a maximum diameter of the head member being larger than or equal to a diameter of the arc of rotation.

13. A compression screw as set forth in claim 12 wherein the modified triangle comprises a separated plurality of flats.

14. A compression screw as set forth in claim 13 wherein the head has three flats which are separated from one another by a hemi-cylindrical flange.

15. A compression screw as set forth in claim 12 wherein the modified triangle comprises flat surfaces that extend in the direction of the longitudinal axis of the screw and wherein the screw head is radially symmetrical.

* * * * *